United States Patent [19]

Berry et al.

[11] Patent Number: 5,230,862
[45] Date of Patent: Jul. 27, 1993

[54] APPARATUS FOR EXTRACORPOREAL BLOOD OXYGENATION

[75] Inventors: Gaylord Berry, Salt Lake City; Shigemasa Osaki; J. D. Mortensen, both of Sandy, all of Utah

[73] Assignee: Cardiopulmonics, Inc., Salt Lake County, Utah

[21] Appl. No.: 746,785

[22] Filed: Aug. 16, 1991

[51] Int. Cl.$^5$ .................... A61M 1/20; B01D 63/06
[52] U.S. Cl. ........................ 422/48; 210/321.79; 210/321.88; 55/16; 55/158
[58] Field of Search ............ 422/48; 55/16, 158; 210/321.79, 321.88; 128/DIG. 3; 261/DIG. 28

[56] References Cited

U.S. PATENT DOCUMENTS

| | | | |
|---|---|---|---|
| 3,422,008 | 1/1969 | McLain | 210/22 |
| 3,505,685 | 4/1970 | Bodell | 3/1 |
| 3,536,611 | 10/1970 | de Filippi et al. | 210/22 |
| 3,794,468 | 2/1974 | Leonard | 23/258.5 |
| 3,856,475 | 12/1974 | Marx | 23/258.5 |
| 4,105,548 | 8/1978 | Baker et al. | 210/23 H |
| 4,158,693 | 6/1979 | Reed et al. | 422/46 |
| 4,180,896 | 1/1980 | Reed et al. | 29/157 R |
| 4,231,878 | 11/1980 | Esmond | 210/321 |
| 4,239,729 | 12/1980 | Hasegawa et al. | 422/48 |
| 4,265,249 | 5/1981 | Schindler et al. | 128/635 |
| 4,268,279 | 5/1981 | Shindo et al. | 55/16 |
| 4,306,018 | 12/1981 | Kirkpatrick | 435/2 |
| 4,352,736 | 10/1982 | Ukai et al. | 55/158 |
| 4,368,124 | 1/1983 | Brumfield | 210/321.3 |
| 4,376,095 | 3/1983 | Hasegawa | 422/46 |
| 4,387,711 | 6/1983 | Merry | 128/207 |
| 4,428,403 | 1/1984 | Lee et al. | 422/47 |
| 4,430,219 | 2/1984 | Kuzumoto et al. | 210/500.2 |
| 4,637,917 | 1/1987 | Reed et al. | 422/46 |
| 4,850,958 | 7/1989 | Berry et al. | 604/26 |

FOREIGN PATENT DOCUMENTS 1280481 11/1961 France .

OTHER PUBLICATIONS

R. Barthelemy, et al., "Total Extracorporeal $CO_2$ Removal in a Pumpless Artery-to-Vein Shunt," *Trans Am Soc Artif Intern Organs* 1982, vol. XVIII, pp. 354-358.

B. R. Bodell, et al., "An Implantable Artificial Lung: Initial Experiments in Animals," *JAMA*, vol. 191, No. 4, Jan. 25, 1965, pp. 125-127.

B. R. Bodell, et al., "A Capillary Membrane Oxygenator," Read at the Forty-third Annual Meeting of The American Association for Thoracic Surgery at Houston, Texas, Apr. 8-10, 1963, pp. 639-650.

P. M. Galletti, et al., "Development of an Implantable Booster Lung," *Trans Am Soc Artif Intern Organs* 1980, vol. XXVI, pp. 573-577.

T. Kolobow, et al., "Carbon Dioxide and the Membrane Artificial Lung: Their Roles in the Prevention and Treatment of Respiratory Failure," *Trans Am Soc Artif Intern Organs* 1982, vol. XVIII, pp. 20-23.

K. Tanishita, et al., "Augmentation of Gas Transfer with Pulsatile Flow in the Coiled Tube Membrane Oxygenator Design," *Trans Am Soc Artif Intern Organs* 1980, vol. XXVI, pp. 561-566.

*Primary Examiner*—James C. Housel
*Assistant Examiner*—Rachel Heather Freed
*Attorney, Agent, or Firm*—Workman Nydegger Jensen

[57] ABSTRACT

An extracorporeal blood oxygenation device having a sealed casing containing a bundle comprised of a plurality of gas permeable tubes for efficient gas transfer. The bundle is woven from tubes having at least two different sizes, at least the smaller diameter tubes being gas permeable. The tubes are relatively non-thrombogenic and are open at each end to an enclosed annular chamber having attached input and output fittings. Oxygen-rich gas flows into one annular chamber through an input fitting before flowing through the gas permeable tubes. Venous blood to be oxygenated is introduced into the sealed casing directly into the center of the bundle for dispersement radially outward through the bundle and across the gas permeable tubes wherein the blood comes in contact with the membrane surface of the gas permeable tubes and exchanges carbon dioxide for oxygen across that surface before being collected from around the perimeter of the bundle for return to the patient.

52 Claims, 6 Drawing Sheets

APPARATUS FOR EXTRACORPOREAL BLOOD OXYGENATION

BACKGROUND

1. Field of the Invention

The present invention relates to methods and apparatus for performing extracorporeal blood oxygenation and in particular to apparatus and methods which utilize membrane oxygenation.

2. The Prior State of the Art

Various heart and circulatory ailments as well as some types of serious injury can adversely affect the flow of blood through the heart and lungs thereby reducing the rate of natural blood gas exchange. Such ailments or injury cause inadequate blood gas exchange which includes both inadequate blood oxygenation and inadequate removal of carbon dioxide ($CO_2$). Also, various types of surgical procedures necessarily require the heart and lungs to be temporarily bypassed. Accordingly, heart/lung bypass circuits have been developed which perform blood oxygenation. Such devices are capable of performing a substantially similar blood gas exchange function to that which naturally occurs in the lungs.

One type of device involves mixing small bubbles of oxygen-rich gas with blood so that the oxygen can be absorbed. Conventional bubble oxygenators developed two primary problems. First, the blood foamed during the gas exchange process. The foam had to be removed before the blood could be returned to the circulatory system. Second, the relatively extended period of time spent by the blood outside the warm confines of a patient's body required a heat exchange mechanism to maintain adequate and essential blood temperature. In the earliest configuration of known blood oxygenation devices, the heat exchanger and the oxygenator were two separate devices built into the same circuit.

Another type of extracorporeal oxygenator employs the use of a gas permeable membrane. The basic concept of operation is essentially the same in all of these membrane oxygenation devices. Blood flows in surface contact with one side of the gas permeable membrane while an oxygen-rich gas flows in surface contact with the other side of the membrane. As the blood flows through the device, the partial pressures of oxygen and carbon dioxide in the blood and in the gas cause oxygen to travel across the gas permeable membrane and to enter the blood. Simultaneously, carbon dioxide exits the blood and travels across the gas permeable membrane. Such a gas permeable membrane allows for the oxygenation of the blood without introducing oxygen bubbles into the blood thereby eliminating the need for defoaming apparatus.

There are several important design characteristics which must be taken into account in order to design an effective membrane oxygenation device. One of the more important design characteristics is the gas exchange performance of the device, characteristic reflects the ability of the device to transfer oxygen to and carbon dioxide from the blood. A well-designed device must have gas exchange characteristics which can meet the metabolic gas exchange requirements of patients up to 200 or 300 pounds in weight while undergoing cardiac surgery or otherwise requiring the use of the heart/lung bypass apparatus.

The gas exchange characteristic of a device is dependent upon several factors. One such factor is termed the "void fraction" of the device. By calculating the total volume within the membrane oxygenator and subtracting from that volume the volume that is taken up by the gas-permeable membrane, one is left with the resultant void volume. The void volume divided by the total volume constitutes the void fraction of the device. In other words, the "void fraction" can be thought of as the amount of space that is available for blood to permeate and flow through the membrane oxygenator. In the case of gas permeable membrane oxygenators which utilize woven bundles of gas permeable tubes, the void fraction is essentially a measurement of the space between the various membrane tubes in relation to the overall space which is taken up by the bundle of gas exchange tubes.

Another important factor which must be taken into account in designing the gas exchange performance characteristic of a device is the hydraulic radius. That factor reflects the dimension of the flow path through which blood has to travel. The void fraction and the hydraulic radius both effect volumetric flow rate, cross-sectional area of the flow path and the distance through which the blood must flow while it is oxygenated. This in turn determines the amount of residence time that the blood spends when travelling through the oxygenator device.

These various design considerations are typically balanced one against the other in an effort to achieve a device which is as small as possible so that the volume of blood which is needed to prime the device is decreased as much as possible, while on the other hand attempting to maintain a relatively high surface area which is available for contact by the blood so that oxygenation can occur as quickly and as efficiently as possible, while also attempting to maintain the void fraction as high as possible so as to not subject the blood to high pressure which may potentially damage the blood, or unduly long residence times.

It has been very difficult in the past to effectively balance the various design considerations and to achieve optimal performance in all of the mentioned areas, namely, low priming volume, high efficiency or gas exchange performance, and low pressure requirements.

BRIEF SUMMARY AND OBJECTS OF THE INVENTION

The present invention seeks to more effectively balance design considerations as noted above. More specifically, the apparatus and method of this invention constitute an important advance in the art of extracorporeal blood gas exchange devices as evidenced by the following or other objects and advantages of the invention.

It is a primary object of the present invention to provide an improved extracorporeal blood oxygenation device which incorporates a bundle woven of gas permeable tubes for membrane oxygenation of blood, and which has a low priming volume, high efficiency or gas exchange characteristics, and low pressure characteristics.

It is another object of the present invention to provide an apparatus containing a bundle woven of gas permeable tubes in such a fashion that the bundle has a relatively high void fraction such that blood residence time and pressure are relatively low.

It is yet another object of the present invention to provide an apparatus containing a bundle woven of gas permeable tubes which maximizes the membrane surface contact area exposed to the blood while still reducing overall volume of the device.

It is yet another object of the present invention to provide an apparatus having a bundle which is woven of gas permeable tubes in such a manner as to minimize the number of junction contact points occurring between individual gas permeable tubes thereby reducing the risk of blood stagnation and clots, while still increasing the available membrane surface contact area exposed to the blood for adequate gas exchange to occur.

These and other objects and features of the present invention will become more fully apparent from the following description and appended claims taken in conjunction with the accompanying drawings, or may be learned by the practice of the invention.

Briefly summarized, the apparatus and method of the present invention are designed for use in surgery or on a routine basis to treat patients with inadequate blood gas exchange rates. In one embodiment of the present invention, the apparatus comprises a sealed casing having a generally cylindrical shaped outer housing with an upper cap member for enclosing one end of the cylindrical housing and a lower cap member for enclosing the other end of the housing. Attached to the end cap members are input and output fittings for the attachment of tubing to allow for the flow of blood and oxygen into and out of the sealed housing. A stopcock is attached to the side of the housing for venting the device during priming. The enclosed housing contains a bundle woven of gas permeable tubes for oxygenating the blood.

The enclosed bundle is woven in a generally circular fashion from solid fibers and/or gas permeable tubes having at least two sizes that differ from one another in outside diameter. The fibers and/or gas permeable tubes are woven over a central spindle which forms a passageway through which the blood can be introduced into the center of the bundle for outward radial dispersement through the bundle and across the membrane tubes.

The input gas is introduced into an annular chamber, which is enclosed by one end cap member. The input gas enters the end cap member through an input fitting which is connected to a source of oxygen-rich gas. This annular chamber is exposed to one end of the bundle of tubes. The oxygen rich gas enters the input annular chamber and flows through the gas permeable tubes to an output annular chamber. The exhaust mixture of carbon dioxide and other gases accumulates at the output annular chamber after flowing through the gas permeable tubes. This exhaust mixture exits the output annular chamber through a fitting connected to an exhaust gas apparatus.

Venous blood in need of oxygenation is introduced into the oxygenation device at a point central to the spindle of the bundle by an attached fitting which enters through the cap member for depositing the blood directly into the spindle. The blood disperses radially outward from the center of the bundle and permeates through the gas permeable tubes. The blood comes in surface contact with the gas permeable membranes and the blood exchanges carbon dioxide for oxygen through the membrane surface of the gas permeable tubes. The oxygen-rich blood accumulates at the outer radius of the bundle and exits the sealed casing through a fitting attached to the casing wall to be returned to the patient.

BRIEF DESCRIPTION OF THE DRAWINGS

In order to more fully understand the manner in which the above-recited advantages and objects of the present invention are obtained, a more particular description of the invention will be rendered by reference to specific embodiments thereof which are illustrated in the appended drawings. Understanding that these drawings depict only one or more embodiments of the invention and are therefore not to be considered limitations in the scope of the invention, the presently preferred embodiments and the presently understood best mode of the invention will be described with additional detail through use of the accompanying drawings in which.

DETAILED DESCRIPTION OF THE PREFERRED EMBODIMENTS

Reference is now made to the drawings wherein like parts are designated with like numerals throughout.

Figure 1:
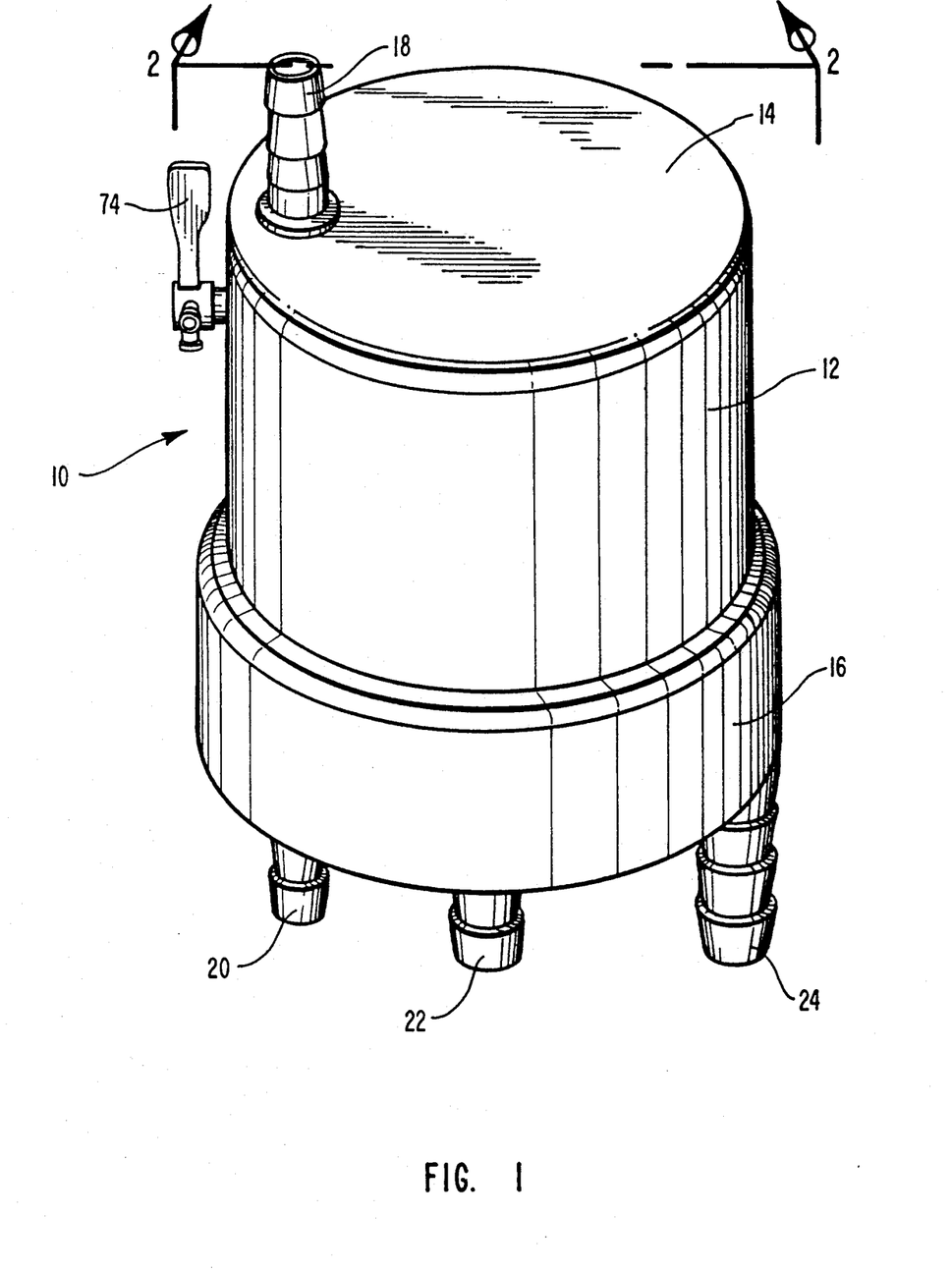
FIG. 1 is a perspective view of one presently preferred embodiment within the scope of the present invention illustrating the sealed casing enclosed by top and bottom end cap members having fittings attached and a stop cock protruding from the side wall of the sealed outer housing.

With reference first to FIG. 1, the apparatus of the present invention is generally designated at 10. In one aspect of the invention, the apparatus is comprised of a means for forming a sealed casing, which in turn is comprised of a gaseous input means for introducing oxygen flow into the sealed casing means, a gaseous output means for removal of carbon dioxide or other exhaust gases from the sealed casing means, a blood input means for introducing blood into the sealed casing means for oxygenation, and a blood output means for returning the oxygenated blood from the sealed casing means to the patient.

Figure 3:
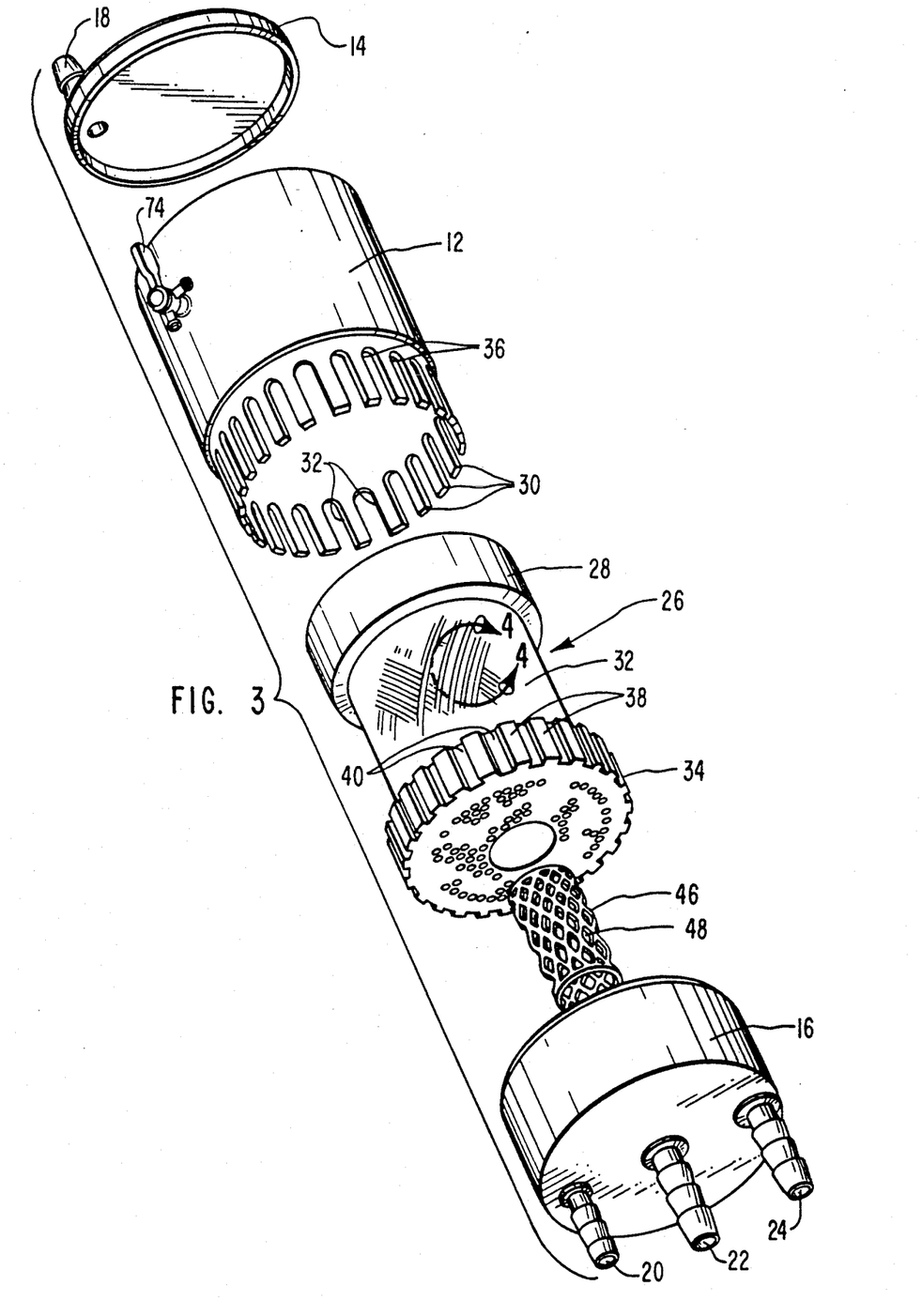
FIG. 3 is an exploded perspective view of the assembly of the embodiment of the present invention as is illustrated in FIG. 1.

As illustrated by way of example and not limitation with respect to the various means of the invention, in the presently preferred embodiment as illustrated in FIGS. 1 and 3 the means for forming the sealed casing is shown as comprising a generally cylindrical outer housing member 12 which is enclosed at the upper end thereof by an upper cap member 14, and which is enclosed at the lower end thereof by a lower cap member 16. On the upper cap member 14 there is formed an exhaust port 18 which may be either open to atmosphere or connected by tubing (not shown) to a source of vacuum (not shown) which draws the exhaust gases, particularly carbon dioxide which has been given up by the blood as it is oxygenated, for removal from the oxygenation device. On the lower cap member, there is formed an inlet gas port 20 which is used for introducing an oxygenation-rich gas into the oxygenation device and which is used for oxygenating the blood by means of the membrane oxygenation process to be described more particularly below. Blood from the patient is introduced through the blood inlet port 22 into the membrane oxygenation device 10 and is returned through the blood outlet port 24 to the patient after the blood has been oxygenated.

Figure 2:
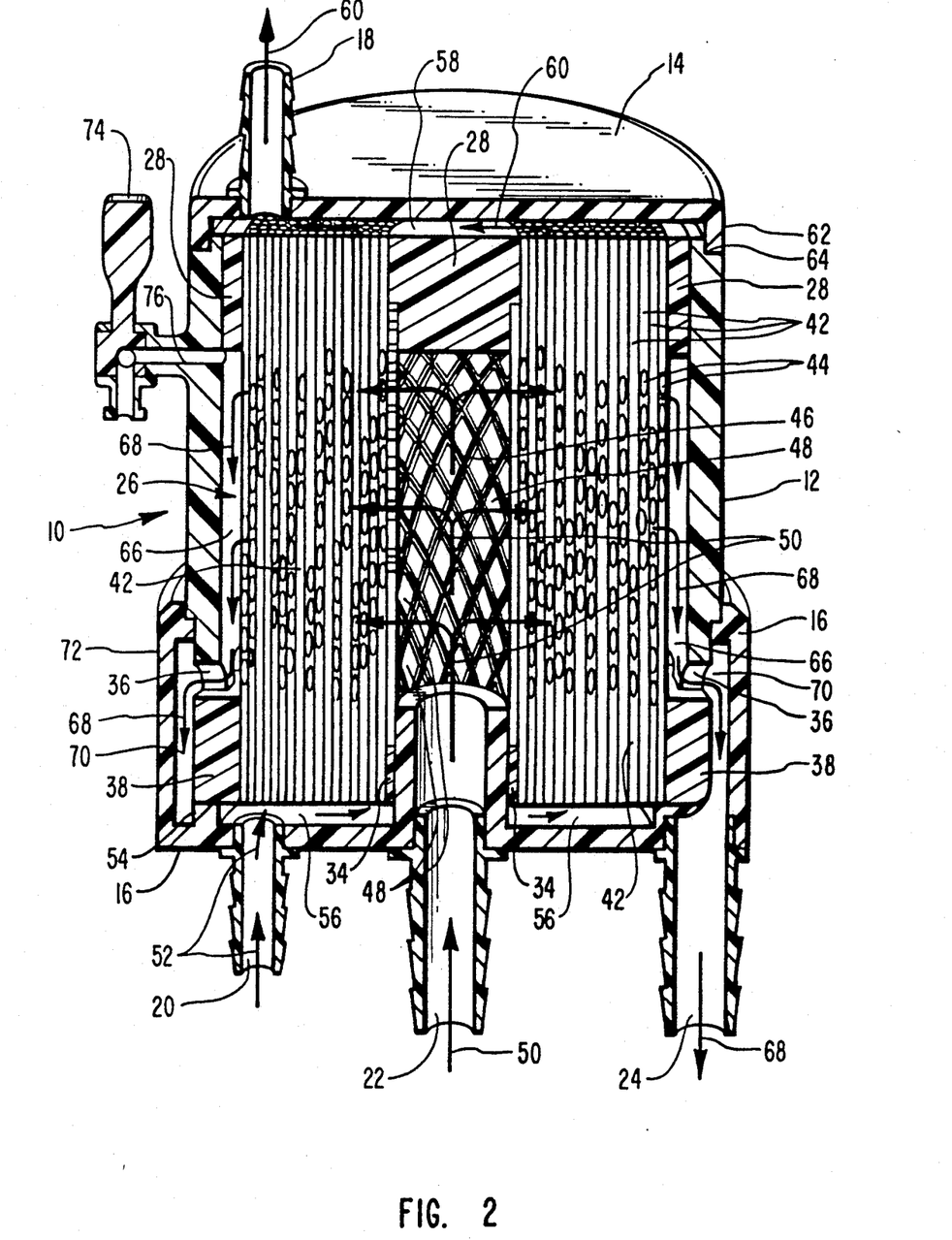
FIG. 2 is a cross-sectional view taken along lines 2—2 of FIG. 1, and schematically shows the sealed outer housing containing the woven bundle of gas permeable tubes with arrows schematically indicating gas and blood flow.

The internal construction of the blood oxygenation device 10 and the manner by which the membrane oxygenation occurs can best be understood by reference to FIGS. 2 and 3 taken together, to which reference is next made. FIG. 2 is a sectional view taken along lines 2—2 of FIG. 1 and FIG. 3 is an exploded perspective view.

In accordance with another aspect of the invention, the membrane oxygenation device 10 comprises a membrane oxygenation means situated within the sealed casing means for oxygenating the blood as the blood permeates through the membrane oxygenation means. As illustrated by way of example in FIGS. 2 and 3, the membrane oxygenation means is comprised of a plurality of solid fibers and/or gas permeable tubes which are woven into a bundle as generally designated at 26. The bundle 26 of gas permeable tubes, when woven, appears much like a ball of twine. The ends of the bundle 26 are then cut at each end so as to open the individual tubes to provide inlet and outlet ends thereof through which the oxygen-rich gas flows into the bundle and from which the carbon dioxide which is taken up from the blood is exhausted, as hereinafter more fully described.

At the upper and lower ends of the bundle 26 the individual gas permeable tubes are secured by a resin-based potting compound so as to firmly secure the bundle 26 within the cylindrical outer housing member 12. Thus, as illustrated in FIGS. 2 and 3, the potting compound which secures the upper end of the gas permeable tubes of bundle 26 is illustrated at reference numeral 28 and is formed as a generally cylindrical collar.

As seen best in FIG. 3, the lower end of the cylindrical outer housing member 12 is comprised of a plurality of fingers 30 which, as hereinafter more fully described, provide openings 32 between them which permit passage of the blood after it has been oxygenated into the blood outlet port 24 for return to the patient. Accordingly, as shown in FIG. 3, the potting compound which is used to secure the lower end of the gas permeable tubes of bundle 26 conforms to the spaces 32 between the individual fingers 30 and fills those spaces 32. The result is that the potting compound, when cured, appears as shown at reference numeral 34. The raised portions 38 constitute the portions of the potting compound which fill in the spaces 32 between the individual fingers 30, whereas the intermediate portions 40 constitute the areas where the potting compound is situated directly behind the individual fingers 30.

It is to be further noted that the raised portions 38 of the cylindrical ring 34 are shorter in length than the overall length of the individual spaces 32, which leaves the upper semi-circular portion 36 of those spaces unobstructed. This is best illustrated in FIG. 2 at reference numeral 36, and it is through this unobstructed space 36 that the blood is permitted to flow out of the cylindrical outer housing member 12 and ultimately through the blood outlet port 24 back to the patient.

As will be described in greater detail in connection with FIGS. 4-6, the bundle 26 is woven from a plurality of gas permeable tubes which differ in size from one another. In FIG. 2, individual tubes are schematically illustrated at reference numeral 42. Furthermore, as hereinafter more fully described, the individual gas permeable tubes 42 are wound on an angle in reference to the horizontal axis of the bundle 26. Since the drawing at FIG. 2 is a cross-sectional view, due to the angle at which the tubes 42 are wound the vertical section of the tubes 42 shows elliptical openings at the point where the plane of the vertical section is taken through the bundle 26, such elliptical openings being schematically illustrated for example at reference numeral 44.

With continued reference to FIGS. 2 and 3 taken together, the bundle 26 of gas permeable tubes 42 is wound upon a central spindle which is illustrated at 46. The spindle 46 preferably comprises a polypropylene mesh which has openings 48 which permits passage of blood therethrough. The potting compound 28 plugs the upper end of spindle 46.

As schematically illustrated by arrows 50 blood enters through the blood inlet port 22 from the patient into the center of the bundle 26 and is then disbursed through the openings 48 of spindle 46 for radial passage through the bundle 26 gas of permeable tubes 42. The blood permeates through the spaces between the individual gas permeable tubes 42, as hereinafter more fully described, so that the blood permeates radially toward the outside of bundle 26. As the blood thus passes through bundle 26 of gas permeable tubes 42, membrane oxygenation occurs.

With particular reference to FIG. 2, oxygen-rich gas is introduced through the gas inlet port 20 as shown schematically by arrows 52. The lower cap member 16 is spaced from the bottom of the cylindrical housing member 12 by means of an annular shoulder 54 thereby forming an annular input chamber 56 between the ends of the gas permeable tubes 42 and the lower cap member 16. Accordingly, oxygen-rich gas enters the annular input chamber 56 and then flows into the ends of the various gas permeable tubes 42 and upwardly through those tubes toward the other end of each of the individual tubes 42. Since the individual tubes 42 are formed from a gas permeable material, the partial pressures of oxygen and carbon dioxide in the blood and in the oxygen-rich gas which are in contact with the tubes on opposite sides of their surface cause the oxygen to pass through the gas permeable tubes 42 and into the oxygen while at the same time carbon dioxide passes from the blood into the interior of the gas permeable tubes 42 and is taken up and then exhausted from the device.

The carbon dioxide and other exhaust gases are collected at the upper end of the device in an annular output chamber 58 which is formed between the upper ends of the gas permeable tubes and the upper cap member 14. The annular output chamber 58 is formed by means of a lip 62 which extends downwardly from the upper cap member 14 and mates with a corresponding shoulder 64 formed in the upper periphery of the cylindrical outer housing member 12. Thus, as schematically shown at arrows 60, the carbon dioxide and other exhaust gases are drawn from the upper end of the gas permeable tubes 42 into the chamber 58 and then out through the gas exhaust port 18 which is connected to a source of suction or vacuum (not shown).

With further reference to FIG. 2, it will be seen that the radial diameter of the bundle 26 of gas permeable tubes 42 is less than the inside diameter of the cylindrical housing member 12. This difference in radial diameter results in an annular blood collection chamber 66 which is formed around the outside of the bundle 26. As the blood which is being oxygenated permeates the bundle 26 of gas permeable tubes 42, the blood flows radially outward and the oxygenated blood is then collected initially in the annular collection chamber 66. The blood then flows through the semi-circular openings 36 which are formed between the top of the individual spaces 32 between each of the fingers 30 (see also FIG. 3) and then into a second annular blood collection chamber 70 which is formed by the upwardly extending vertical sides 72 of the lower cap member 16. From the lower annular collection chamber 70 the oxygenated blood, which is schematically represented by arrows 68, then flows into the blood outlet port 24 and back to the patient.

As will be appreciated from the foregoing description, in the illustrated, preferred embodiment the gaseous input means for introducing oxygen flow into the sealed casing is comprised of the combination of the gas inlet port 20 the annular input chamber 56. The gaseous output means for removal of carbon dioxide and other exhaust gases from the sealed casing are comprised, in the illustrated example, by the combination of the gas outlet port 18 and the annular output chamber 58 which is formed at the other end of the device. The blood input means for introducing blood into the sealed casing for oxygenation is comprised in the illustrated example by the combination of the blood inlet port 22, and the mesh spindle 46 through which blood is introduced into the bundle of gas permeable tubes 42. The blood output means for returning oxygenated blood from the sealed casing is comprised in the illustrated embodiment by the combination of the first annular blood collection chamber 66, semi-circular openings 36 provided at the top of each space 32, the second, lower annular blood collection chamber 70 and the blood outlet port 24.

It is to be understood and appreciated that each of the stated means could be designed in a variety of different ways while still performing the same functions as described with respect to each such means, and such variations are therefore intended to be within the scope of the invention as broadly described and claimed.

With further reference to FIG. 2, the cylindrical outer housing member 12 also comprises a stop cock 74 which communicates by means of passage 76 to the annular blood collection chamber 66. The stop cock 74 is designed to permit priming of the device so that when the device is first filled with blood all of the air inside of the device can be thoroughly expelled by opening the stop cock 74 and then once the device is completely primed and all of the air inside of the device has been removed the stop cock 74 can be closed.

In connection with the potting agent that is used to secure the upper and lower ends of the bundle 26, the particular compound that is selected will depend upon the compound's viscosity, surface tension and spreadability. Polyurethane is one presently preferred potting compound but other suitable compounds include epoxies, silicones or other thermosetting resins.

Since the gas permeable tubes are in contact with the blood as the blood permeates radially outwardly through the bundle 26, it is important to minimize thrombosis. Therefore, it is also preferable that the individual gas permeable tubes 42 be constructed with a thrombo-resistant coating. Presently preferred examples of such thrombo-resistant coatings are disclosed in copending U.S. patent application Ser. No. 215,014 filed Jul. 5, 1988 and Ser. No. 509,063 filed Apr. 12, 1990, which are incorporated herein by reference.

One presently preferred material for constructing the sealed casing, including both the outer cylindrical housing 12 and the end cap members 14 and 16, is polycarbonate due its to compatibility with related polyurethane potting compounds. Other possible suitable and inexpensive materials for constructing the sealed casing are polystyrene and acrylonitrile-butadiene-styrene. It will be appreciated that the materials are not limiting with respect to the scope of the invention, but are to be selected having due consideration for keeping cost as low as possible since the device 10 is a disposable device.

Figure 4:
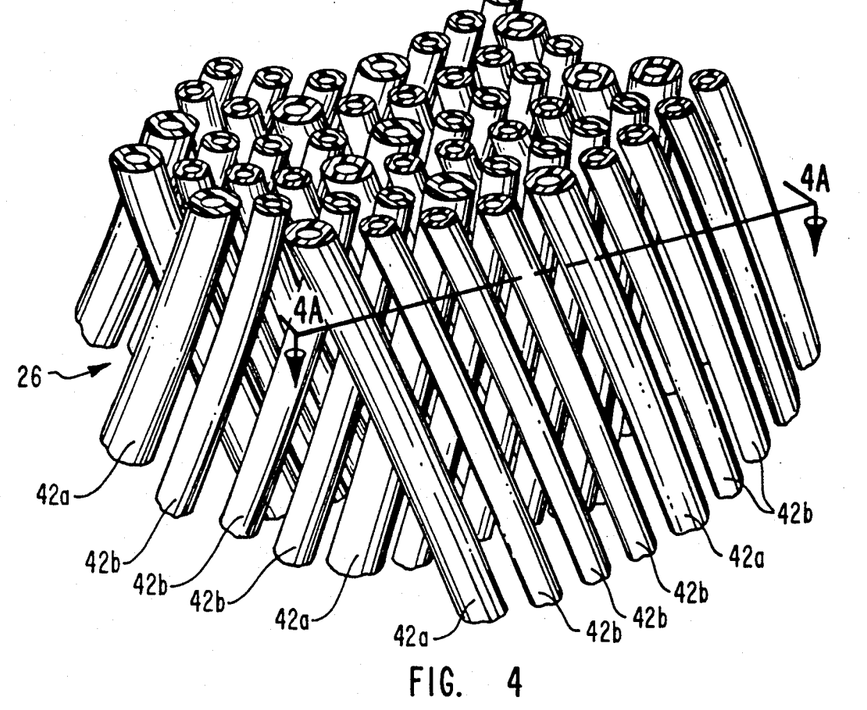
FIG. 4 is an enlarged perspective view shown partially in cross-section, illustrating a small piece of the woven bundle, so as to depict the larger diameter tubes interwoven with the smaller diameter tubes in the preferred weaving ratio.
Figure 5:
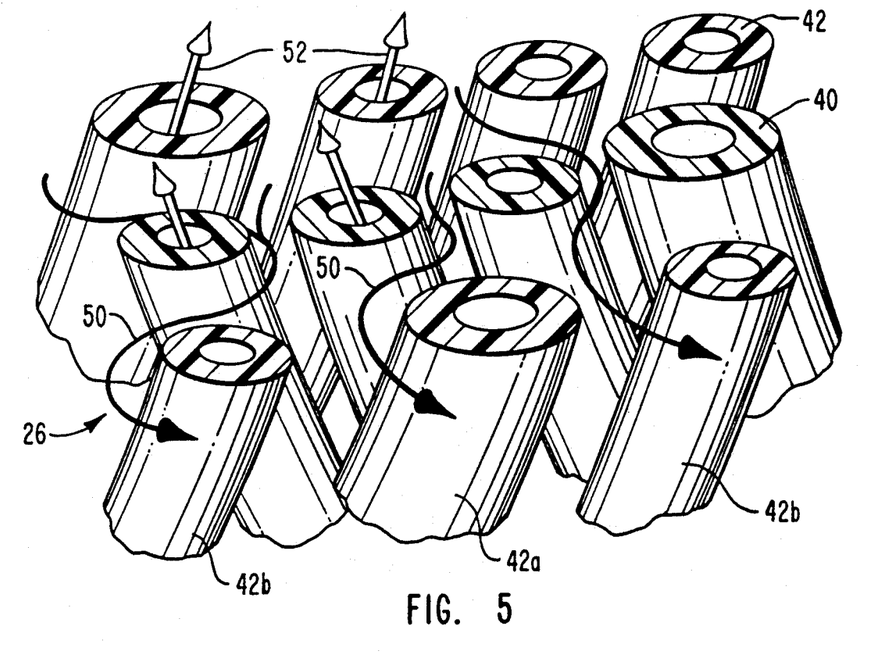
FIG. 5 is an enlarged cross-sectional view of the gas permeable tubes, illustrated in FIG. 4, showing the direction the blood takes while permeating through the bundle in contact with the tube membrane surfaces.
Figure 6:
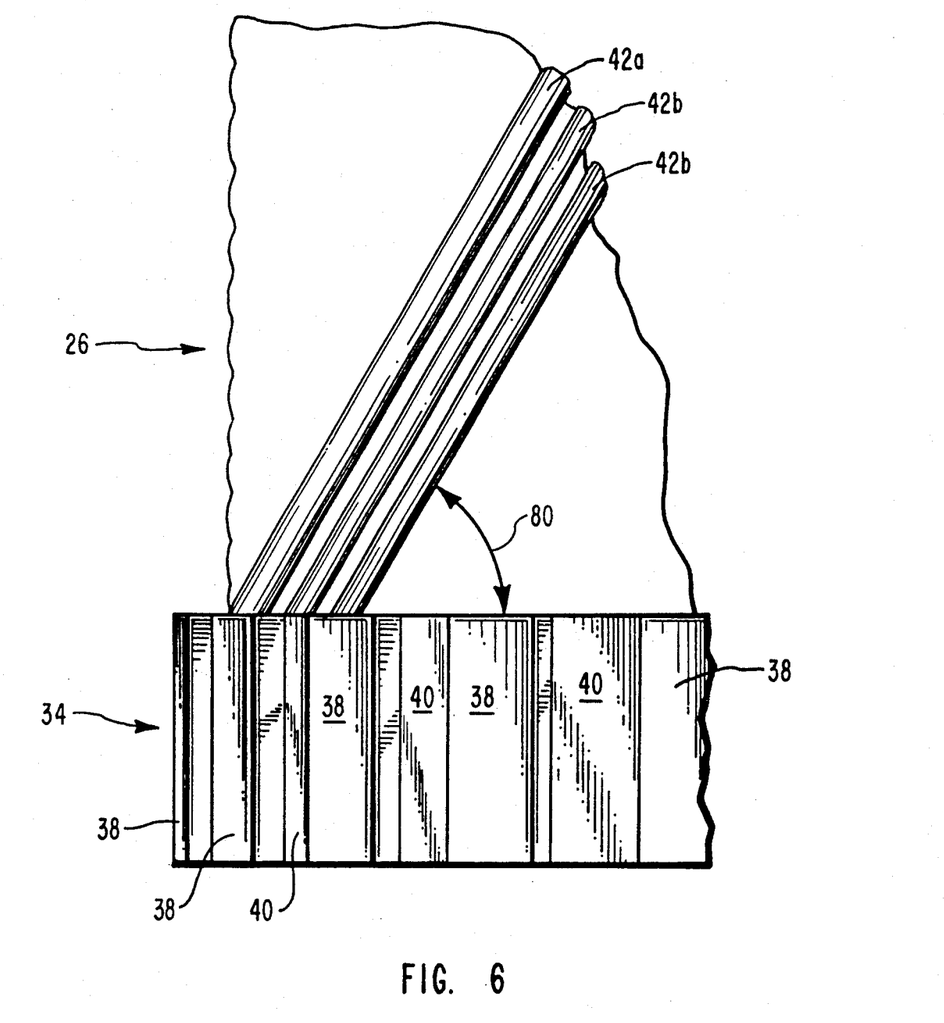
FIG. 6 is a schematic illustration of the weaving angle drawn relative to an axis taken 90 degrees to the center line of the spindle.

In yet another important aspect of the invention, bundle 26 is woven over spindle 46 from gas permeable tubes 42 having at least two sizes that differ from one another in outside diameter, as illustrated in FIG. 4–6. By way of example, the larger diameter tubes 42a are preferably within a range of 250 to 400 microns outside diameter and the smaller diameter tubes 42b are within a range of 150 to 300 microns outside diameter.

Figure 4A:
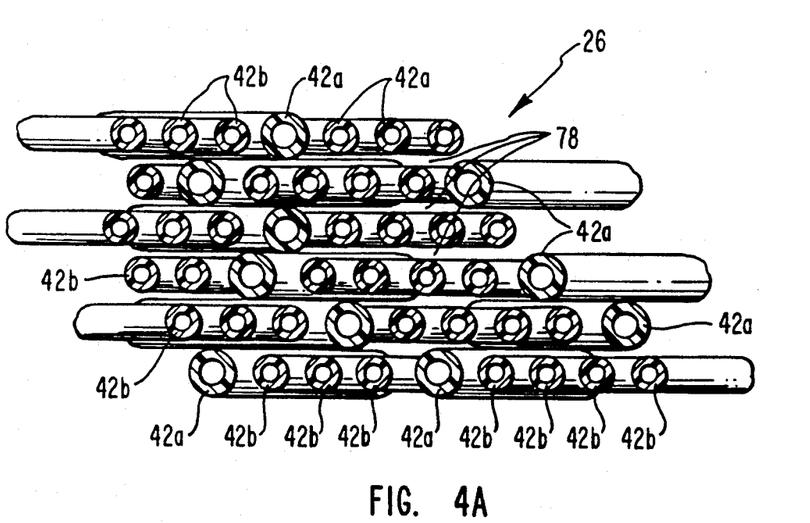
FIG. 4A is a cross-sectional view taken along lines 4A—4A of FIG. 4.

As best illustrated in FIG. 4A, this difference in size results in the larger diameter tubes 42a contacting essentially only other larger diameter tubes 42a so as to significantly reduce the number of tube-to-tube junction contact points. Accordingly, as further best illustrated in FIG. 4a the smaller diameter tubes 42b are essentially free floating between the larger diameter tubes 42a, as shown by the space 78 which separates the smaller diameter tubes 42b from both other smaller diameter tubes 42b as well as from the larger diameter tubes 42a. In other words, there is contact essentially only between the larger diameter tubes 42a.

The use of gas permeable tubes of two differing sizes when weaving the bundle 26 results in several significant advantages. First, as noted above, junction contact points between the gas permeable tubes is significantly reduced in number. This has the advantage of minimizing potential stagnation areas and reducing blood clotting as the blood flows through the tubes. Thus, as schematically illustrated by the arrows 50 in FIG. 5, as the blood flows through the gas permeable tubes 42 the blood is permitted to freely flow everywhere except between those points where the larger diameter tubes 42a contact one another.

Another advantage is that this increases the void fraction or the available space through which the blood can flow, and also reduces the pressure drop that is imposed on the blood as it passes through the bundle 26 as it is oxygenated. A further advantage is that the overall size of the device can therefor be smaller and yet the surface area of the gas permeable membrane is still relatively high. The result is that the bundle 26 of gas permeable tubes 42, when woven in a manner using tubes of differing sizes as illustrated in the presently preferred embodiment, provides a membrane oxygenation device which has high efficiency or gas exchange characteristics which are very good, which has a lower priming volume because of the reduced size and which also reduces the pressure drop which occurs as the blood flows from inside the bundle 26 to outside of the bundle in the manner illustrated in FIG. 2.

In accordance with the inventive concept disclosed herein, it is contemplated and is intended to be within the scope of the present invention that gas permeable tubes 42 having more than two differing sizes could be used. However, the presently preferred embodiment is to use only two different sizes and specifically, to use them in a weaving ratio of seven smaller diameter tubes to two larger diameter tubes. In other words, for every two revolutions when winding the bundle 26 which are made with the larger diameter tubes 42a, there will be seven revolutions completed with respect to the smaller diameter tubes 42b.

It is also within the scope of the invention to use a combination of solid fibers and gas permeable tubes. Thus, the tubes 42a of larger diameter could be replaced by solid fibers. Thus, as used herein, the term "tubes" is intended to embrace any combination of solid fibers used with gas permeable tubes, as well as any combination of larger and smaller diameter gas permeable tubes.

Also in connection with weaving the tubes 42 so as to form the bundle 26, a particular winding angle must be used. As illustrated schematically in FIG. 6, the winding angle is described herein in reference to the horizontal axis and in the illustrated embodiment is preferably sixty degrees as schematically represented by the arrow 80 in FIG. 6, although the winding angle could be within a range of 1 to 89 degrees. Similarly, while a preferred weaving ratio consists of seven smaller diameter tubes to two larger tubes, the weaving ratio could be anywhere within a range of from 1 to 1000 small diameter tubes, and from 1 to 1000 larger diameter tubes.

The winding angle and weaving ratio are matters of design choice and are preferably selected so that the total void fraction of the device is maintained within a range of from 45% to 55%, and preferably between 49% to 51%.

The present invention may be embodied in other specific forms without departing from the spirit of this invention or its essential characteristics. The described embodiments are to be considered, in all respects, as illustrative and not restrictive. The scope of the invention is, therefore, indicated by the appended claims rather than by the foregoing description. All changes which come within the meaning and range of equivalency of the foregoing claims are to be embraced within their scope.

What is claimed is:

1. A device for blood gas exchange comprising:
   (a) means for forming a sealed casing comprising:
       gaseous input means for introducing oxygen flow into said sealed casing means;
       gaseous output means for removal of carbon dioxide from said sealed casing means;
       blood input means for introducing blood into said sealed casing means for oxygenation; and
       blood output means for returning oxygenated blood from said sealed casing means; and
   (b) membrane oxygenation means situated within said sealed casing means for oxygenating blood as blood permeates through said membrane oxygenation means, said membrane oxygenation means comprising a plurality of tubes woven together to form a bundle such that blood entering said sealed casing means will radially permeate through said bundle as blood flows from said blood input means to said blood output means, at least some of said tubes being gas permeable and opened at one end of said bundle to said gaseous input means, and opened at an opposite end of said bundle to at least some of said gaseous output means so that oxygen will flow through at least some of said tubes and oxygenate blood as blood radially permeates through said bundle, said bundle woven in a generally circular fashion from individual, separate tubes, each of which are wound generally in layers, and wherein each tube is separate and essentially parallel to each of the other tubes in the layer, and the parallel tubes having a weaving ratio due to alternating tubes having at least two sizes that differ from one another in outside diameter as they are wound to form said bundle.

2. A device as defined in claim 1 wherein said means for forming said sealed casing comprises:
   (a) a generally cylindrical outer housing member;
   (b) an upper cap member for enclosing one end of said outer housing member; and
   (c) a lower cap member for enclosing another end of said outer housing member.

3. A device as defined in claim 2 wherein said gaseous input means comprises:
   (a) an input port through one of said upper and lower cap members; and
   (b) an annular input chamber formed between the ends of said tubes and said one of said upper and lower cap members.

4. A device as defined in claim 3 wherein said gaseous output means comprises:
   (a) an output port through the other of said upper and lower cap members; and
   (b) an annular output chamber formed between the ends of said gas permeable tubes and said other of said upper and lower cap members.

5. A device as defined in claim 2 further comprising a spindle means for defining a support onto which said bundle is woven and for defining a central passageway through which blood is introduced into the center of said bundle for radial dispersement through said bundle.

6. A device as defined in claim 5 wherein said spindle means comprises a tubular polypropylene mesh.

7. A device as defined in claim 5 wherein said blood input means comprises a blood inlet port through one of said upper and lower cap members, said blood inlet port situated so as to communicate blood to said spindle means.

8. A device as defined in claim 5 wherein said blood output means comprises a first annular chamber formed between said bundle and said outer housing member.

9. A device as defined in claim 8 further comprising means for venting said first annular chamber to atmospheric pressure.

10. A device as defined in claim 9 wherein said means for venting said first annular chamber comprises a stopcock joined to said outer housing member.

11. A device as defined in claim 8 wherein said blood output means comprises:
    (a) a blood outlet port through one of said upper and lower cap members; and
    (b) a second annular chamber in fluid communication between said first annular chamber and said blood outlet port.

12. A device as defined in claim 1 wherein said tubes or differing sizes are sized in relation to one another such that said larger diameter tubes are within a range of 250 to 400 microns outside diameter and said smaller diameter tubes are within a range of 150 to 300 microns outside diameter.

13. A device as defined in claim 1 wherein said bundle is woven such that the weaving ratio consists of from 1 to 1000 smaller diameter tubes, and from 1 to 1000 larger diameter tubes.

14. A device as defined in claim 1 wherein said bundle is woven such that the weaving ratio is 7 smaller diameter tubes to 2 larger diameter tubes.

15. A device as defined in claim 1 wherein said bundle is woven such that a winding angle is within a range of 1 to 89 degrees.

16. A device as defined in claim 1 wherein said bundle is woven such that a winding angle is 60 degrees.

17. A device as defined in claim 1 wherein said bundle has a total void fraction within a range of 45% to 55%.

18. A device as defined in claim 1 wherein said bundle has a total void fraction between 49% and 51%.

19. A device as defined in claim 1 wherein said larger diameter tubes are firmly in surface contact with essentially others of only said larger diameter tubes, so as to essentially limit the number of contact points between said larger and said smaller diameter tubes to said contact between said larger diameter tubes.

20. A device for blood gas exchange comprising:
   (a) means for forming a sealed casing comprising:
      gaseous input means for introducing oxygen flow into said sealed casing means;
      gaseous output means for removal of carbon dioxide from said sealed casing means;
      blood input means for introducing blood into said sealed casing means for oxygenation; and
      blood output means for returning oxygenated blood from said sealed casing means; and
   (b) membrane oxygenation means situated within said sealed casing means for oxygenating blood as blood permeates through said membrane oxygenation means, said membrane oxygenation means comprising a plurality of gas permeable tubes woven together to form a bundle such that blood entering said sealed casing means will radially permeate through said bundle as blood flows from said blood input means to said blood output means, said tubes opened at one end of said bundle to said gaseous input means, and opened at an opposite end of said bundle to said gaseous output means so that oxygen will flow through said tubes and oxygenate blood as blood radially permeates through said bundle, said bundle woven in a generally circular fashion from individual, separate, gas permeable individual, separate tubes, each of which are wound generally in layers, and wherein each tube is separate and essentially parallel to each of the other tubes in the layer, and the parallel tubes having a weaving ratio due to alternating tubes having at least two sizes that differ from one another in outside diameter as they are wound to form said bundle, such that said bundle has a total void fraction within a range of 45% to 55%.

21. A device as defined in claim 20 wherein said means for forming said sealed casing comprises:
   (a) a generally cylindrical outer housing member;
   (b) an upper cap member for enclosing one end of said outer housing member; and
   (c) a lower cap member for enclosing another end of said outer housing member.

22. A device as defined in claim 21 wherein said gaseous input means comprises:
   (a) an input port through one of said upper and lower cap members; and
   (b) an annular input chamber formed between the ends of said gas permeable tubes and said one of said upper and lower cap members.

23. A device as defined in claim 22 wherein said gaseous output means comprises:
   (a) an output port through the other of said upper and lower cap members; and
   (b) an annular output chamber formed between the ends of said gas permeable tubes and said other of said upper and lower cap members.

24. A device as defined in claim 21 further comprising a spindle means for defining a support onto which said bundle is woven and for defining a central passageway through which blood is introduced into the center of said bundle for radial dispersement through said bundle.

25. A device as defined in claim 24 wherein said spindle means comprises a tubular polypropylene mesh.

26. A device as defined in claim 24 wherein said blood input means comprises a blood inlet port through one of said upper and lower cap members, said blood inlet port situated so as to communicate blood to said spindle means.

27. A device as defined in claim 24 wherein said blood output means comprises a first annular chamber formed between said bundle and said outer housing member.

28. A device as defined in claim 27 further comprising means for venting said first annular chamber to atmospheric pressure.

29. A device as defined in claim 28 wherein said means for venting said first annular chamber comprises a stopcock joined to said outer housing member.

30. A device as defined in claim 27 wherein said blood output means comprises:
   (a) a blood outlet port through one of said upper and lower cap members; and
   (b) a second annular chamber in fluid communication between said first annular chamber and said blood outlet port.

31. A device as defined in claim 20 wherein said gas permeable tubes of differing sizes are sized in relation to one another such that said larger diameter tubes are within a range of 250 to 400 microns outside diameter and said smaller diameter tubes are within a range of 150 to 300 microns outside diameter.

32. A device as defined in claim 31 wherein said bundle is woven such that the weaving ratio consists of from 1 to 1000 smaller diameter tubes, and from 1 to 1000 larger diameter tubes.

33. A device as defined in claim 20 wherein said bundle is woven such that the weaving ratio is 7 smaller diameter tubes to 2 larger diameter tubes.

34. A device as defined in claim 32 wherein said bundle is woven such that a winding angle is within a range of 1 to 89 degrees.

35. A device as defined in claim 20 wherein said bundle is woven such that a winding angle is 60 degrees.

36. A device as defined in claim 20 wherein said bundle has a total void fraction between 49% and 51%.

37. A device as defined in claim 36 wherein said larger diameter tubes are firmly in surface contact with essentially others of only said larger diameter tubes, so as to essentially limit the number of contact points between said larger and said smaller diameter tubes to said contact between said larger diameter tubes.

38. A device for blood gas exchange comprising:

(a) means for forming a sealed casing comprising: a generally cylindrical outer housing member;
an upper cap member for enclosing one end of said outer housing member; and
a lower cap member for enclosing the opposite end of said sealed outer housing member;

(b) membrane oxygenation means situated within said sealed casing means for oxygenating blood as blood permeates through said membrane oxygenation means, said membrane oxygenation means comprising a plurality of gas permeable tubes woven together to form a bundle such that blood entering said sealed casing means will radially permeate through said bundle as blood flows from a blood input means to a blood output means, said tubes opened at one end of said bundle to a gaseous input means, and opened at an opposite end of said bundle to a gaseous output means so that oxygen will flow through said tubes and oxygenate blood as blood radially permeates through said bundle, said bundle woven in a generally circular fashion from individual, separate, gas permeable individual, separate tubes, each of which are wound generally in layers, and wherein each tube is separate and essentially parallel to each of the other tubes in the layer, and the parallel tubes having a weaving ratio due to alternating tubes having at least two sizes that differ from one another in outside diameter as they are wound to form said bundle, such that said bundle has a total void fraction within a range of 45% to 55%;

(c) a spindle means upon which said bundle is woven for introducing said blood into the center of said bundle for radial dispersement through said bundle;

(d) gaseous input means for introducing oxygen flow into said sealed casing means comprising:
an input port through one of said upper and lower cap members for introducing oxygen flow into said sealed casing; and
an annular input chamber formed between the ends of said gas permeable tubes and said opposite end of said upper and lower cap members;

(e) gaseous output means for removal of carbon dioxide from said sealed casing means comprising:
an output port through the opposite end of said upper and lower cap members for removal of carbon dioxide from said sealed casing; and
an annular output chamber formed between the ends of said gas permeable tubes and said opposite end of said upper and lower cap members;

(f) blood input means for introducing blood into said sealed casing means for oxygenation comprising a blood input port through one of said upper and lower cap members for a blood inlet port situated so as to communicate blood to said spindle means; and (g) blood output means for returning said oxygenated blood from said sealed casing means comprising:
a blood output port through one of said upper and lower cap members for returning said oxygenated blood from said sealed casing;
first annular chamber formed between said bundle and said sealed outer housing member; and
a second annular chamber in fluid communication between said first annular chamber and said blood output port.

39. A device as defined in claim 38 wherein said tubes of differing sizes are sized in relation to one another such that said larger diameter tubes are within a range of 250 to 400 microns outside diameter, and said smaller diameter tubes are within a range of 150 to 300 microns outside diameter.

40. A device as defined in claim 39 wherein said bundle is woven such that the weaving ratio consists of from 1 to 1000 smaller diameter tubes, and from 1 to 1000 larger diameter tubes.

41. A device as defined in claim 40 wherein said bundle is woven such that a winding angle is within a range of 1 to 89 degrees.

42. A device as defined in claim 41 wherein said larger diameter tubes are firmly in surface contact with essentially others of only said larger diameter tubes, so as to essentially limit the number of contact points between said larger and said smaller diameter tubes to said contact between said larger diameter tubes.

43. A device as defined in claim 38 wherein said bundle is woven such that the weaving ratio is 7 smaller diameter tubes to 2 larger diameter tubes.

44. A device as defined in claim 38 wherein said bundle is woven such that a winding angle is 60 degrees.

45. A device as defined in claim 38 wherein said bundle has a total void fraction between 49% and 51%.

46. A device as defined in claim 38 further comprising means for venting said first annular chamber to atmospheric pressure.

47. A device as defined in claim 46 wherein said means for venting said first annular chamber comprises a stopcock joined to said outer housing member.

48. A device as defined in claim 46 wherein said spindle means comprises a tubular polypropylene mesh around which said bundle of said gas permeable tubes of differing sizes is woven.

49. A device for blood gas exchange comprising:
(a) means for forming a sealed casing comprising:
a generally cylindrical outer housing member;
an upper cap member for enclosing one end of said outer housing member; and
a lower cap member for enclosing the opposite end of said sealed outer housing member;

(b) membrane oxygenation means situated within said sealed casing means for oxygenating blood as blood permeates through said membrane oxygenation means, said membrane oxygenation means comprising a plurality of individual, separate, gas permeable tubes woven together to form a bundle wherein the individual separate tubes are wound generally in layers such that each of the tubes in the layer are essentially parallel and have a weaving ratio due to alternating tube having at least two sizes that differ from one another in outside diameter, such that blood entering said sealed casing means will radially permeate through said bundle as blood flows form a blood input means to a blood output means, said gas permeable tubes comprising larger diameter tubes within a range of 250 to 400 microns outside diameter, and smaller diameter tubes within a range of 150 to 300 microns outside diameter, and said tubes open at one end of said bundle to a gaseous input means, and open at an opposite end of said bundle to a gaseous output means so that oxygen will flow through said tubes and oxygenate blood as blood radially permeates through said bundle, and said tubes having a total void fraction within a range of 45% to 55%, said bundle woven such that said larger diameter tubes are firmly in surface contact with essentially others of only said larger diameter tubes, so as to essentially limit the number of contact points between said larger and said smaller diameter tubes to said contact between said larger diameter tubes, and (c) spindle means for introducing blood into the center of said bundle for radial dispersement through said bundle, said spindle means comprising a tubular polypropylene mesh around which said bundle of said gas permeable tubes of differing sizes is woven upon which said bundle is woven;

(d) gaseous input means for introducing oxygen flow into said sealed casing means comprising:
an input port through one of said upper and lower cap members for introducing oxygen flow into said sealed casing; and
an annular input chamber formed between the ends of said gas permeable tubes and said opposite end of said upper and lower cap members;

(e) gaseous output means for removal of carbon dioxide from said sealed casing means comprising:
an output port through the opposite end of said upper and lower cap members for removal of carbon dioxide from said sealed casing; and
an annular output chamber formed between the ends of said gas permeable tubes and said opposite end of said upper and lower cap members;

(f) blood input means for introducing blood into said sealed casing means for oxygenation comprising a blood inlet port through one of said upper and lower cap members and situated so as to communicate blood to said spindle means;

(g) blood output means for returning oxygenated blood from said sealed casing means comprising:
a blood outlet port through one of said upper and lower cap members for returning oxygenated blood from said sealed casing;
a first annular chamber formed between said bundle and said sealed outer housing member; and
a second annular chamber in fluid communication between said first annular chamber and said blood outlet port; and (h) venting means for venting said first annular chamber to atmospheric pressure, said venting means comprises a stopcock jointed to said outer housing member.

50. A device as defined in claim 49 wherein said bundle is woven such that a winding angle is 60 degrees.

51. A device as defined in claim 49 wherein said bundle has a total void fraction between 49% and 51%.

52. A device as defined in claim 49 wherein said bundle has a weaving ratio of 7 smaller diameter tubes to 2 larger diameter tubes.

* * * * *

UNITED STATES PATENT AND TRADEMARK OFFICE
CERTIFICATE OF CORRECTION

PATENT NO. : 5,230,862
DATED : July 27, 1993
INVENTOR(S) : GAYLORD BERRY et al.

It is certified that error appears in the above-indentified patent and that said Letters Patent is hereby corrected as shown below:

Column 1, line 59, after "device," insert --sometimes referred to as the efficiency of the device. This--
Column 2, line 21, "effect" should be --affect--
Column 8, line 59, "therefor" should be --therefore--
Column 16, line 18, "comprises" should be --comprising--

Signed and Sealed this

Twelfth Day of July, 1994

Attest:

BRUCE LEHMAN

*Attesting Officer*          Commissioner of Patents and Trademarks